(12) United States Patent
Murata

(10) Patent No.: US 7,892,801 B2
(45) Date of Patent: Feb. 22, 2011

(54) PROCESS FOR ENHANCING THE ACTIVITY OF GLUCOSE OXIDASE

(75) Inventor: Yusuke Murata, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 855 days.

(21) Appl. No.: 11/806,102

(22) Filed: May 30, 2007

(65) Prior Publication Data

US 2007/0298480 A1    Dec. 27, 2007

(30) Foreign Application Priority Data

Jun. 8, 2006   (JP) .............................. 2006-159714

(51) Int. Cl.
*C12N 11/14* (2006.01)
*C12N 9/96* (2006.01)
*C12N 9/04* (2006.01)
*C12Q 1/54* (2006.01)

(52) U.S. Cl. .................. 435/176; 435/14; 435/188; 435/190; 435/817

(58) Field of Classification Search .................. None
See application file for complete search history.

(56) References Cited

U.S. PATENT DOCUMENTS

| | | | | |
|---|---|---|---|---|
| 4,025,667 A * | 5/1977 | Tomb et al. | ................. | 427/215 |
| 7,267,971 B2 * | 9/2007 | Thakur et al. | ............... | 435/176 |
| 7,688,056 B2 * | 3/2010 | Murata | .................... | 324/76.11 |
| 7,741,069 B2 * | 6/2010 | Murata | ....................... | 435/26 |
| 2002/0015985 A1 | 2/2002 | Takahashi et al. | ........... | 435/180 |
| 2004/0092003 A1 * | 5/2004 | Boschetti et al. | ......... | 435/287.1 |
| 2007/0148044 A1 | 6/2007 | Murata | .................... | 422/82.01 |

FOREIGN PATENT DOCUMENTS

| | | |
|---|---|---|
| JP | 2000-139459 | 5/2000 |
| JP | 2002-95471 | 4/2002 |

* cited by examiner

*Primary Examiner*—David M Naff
(74) *Attorney, Agent, or Firm*—Fitzpatrick, Cella, Harper & Scinto

(57) ABSTRACT

Effective activation of a biological material such as an enzyme has been demanded. The present invention provides a process for activating a biological material which includes providing a porous material having mesopores; immobilizing a biological material on the pore wall which forms the mesopores; and enhancing the relative activity of the biological material by heating the porous material on which the biological material is immobilized at the optimal temperature and above of the biological material and an apparatus therefor.

6 Claims, 9 Drawing Sheets

PROCESS FOR ENHANCING THE ACTIVITY OF GLUCOSE OXIDASE

BACKGROUND OF THE INVENTION

1. Field of the Invention

The present invention relates to a process and an apparatus for activating a biological material. More specifically, the present invention relates to a process for activating a biological material comprising immobilizing a biological material to a porous material and heating the structure body at the optimal temperature and above of the biological material thereby activating the biological material immobilized in the porous material.

2. Description of the Related Art

Generally, a biological material exemplified by a protein such as an enzyme exhibits only lower activity at a temperature exceeding the optimal temperature than the activity at the optimal temperature of the biological material, at which the biological material can develop the function most adequately. It is also known that when a biological material is exposed to a temperature not lower than a certain temperature, it loses the activity due to the changes of the spacial configuration. The temperature of such heat inactivation is different among the kinds of protein, but the activity tends to be inactivated when heated to around 50° C. in the case of proteins having the optimal temperature at or around room temperature. Proteins stable at high temperatures are also known, and generally, such heat-resistant proteins have higher optimal temperatures.

Conditions of higher temperature should be often used depending on the conditions to be used for each protein. In such cases, it is common to use heat-resistant proteins as mentioned above. However, there are cases that heat resistance is not known or the heat resistance, even if it is known, does not meet the conditions to be used. Various kinds of methods have been conventionally studied to handle such proteins easily as well as stably. One of these methods includes supporting a protein on the solid surface, and can be exemplified by the technology which has been put to practical use by immobilizing enzymes and the like.

Various materials such as silica produced by sol-gel method, fused quartz, porous inorganic materials, porous organic polymer materials are used for immobilizing a biological material such as protein. In late years immobilization on mesoporous materials formed with molecular assembly of surfactant as a mold, particularly mesoporous silica has been proposed. Such technique is described in Japanese Patent Application Laid-Open Nos. 2000-139459 and 2002-095471. Effects such as improvement in the collection ratio and heat-resistance of enzyme by using these various kinds of immobilization methods have been reported.

The immobilization method mentioned above limits the degree of freedom of the protein structure since it immobilizes proteins on the surface or the inside of a solid. Accordingly there was a problem that activity per protein molecule is extremely low compared with proteins in a buffer solution in which they have higher degree of freedom. Methods to stabilize proteins against heat include a method of synthesizing a protein having a high optimal temperature while genetically introducing a variation to, but it is a technique only known for extremely limited kinds of proteins and is not applicable to various kinds of proteins.

The present invention has been achieved in view of the above-mentioned problems and an object thereof is to provide a process and an apparatus for effectively activating a biological material such as a protein.

SUMMARY OF THE INVENTION

The present invention is directed to a process for activating a biological material which comprises the steps of: providing a porous material having mesopores; immobilizing a biological material on a pore wall which forms the mesopores; and enhancing the relative activity of the biological material by heating the porous material on which the biological material is immobilized at a temperature of an optimal temperature for the biological material or more.

The process for activating a biological material can comprise further the step of coating the surface of the pore wall with a material different from a constituent of the pore wall before the immobilizing step, the different material intervening between the biological material and the porous wall in the immobilizing step. The different material can be zirconium oxide.

The optimal temperature can range from 50° C. to 90° C.

The porous material can contain silicon or the porous material consists of silica.

The porous material can have at least one diffraction peak in an angle domain corresponding to a structural period of 1 nm or more in X-ray diffraction method.

The immobilization of the biological material on the pore wall can be achieved by any one selected from the group consisting of electrostatic interaction, van der waals force, hydrogen bond and covalent bond.

The present invention is directed to an apparatus comprising a porous material having mesopores, a biological material immobilized on a pore wall of the mesopores and a heating unit for heating the porous material and the biological material.

The heating can be performed at a temperature of an optimal temperature for the biological material or more. The optimal temperature can range from 50° C. to 90° C.

In the apparatus, a material different from a constituent of the pore wall can intervene between the biological material and the porous wall. The different material can be zirconium oxide.

The porous material can contain silicon or the porous material consists of silica.

The mesopore can have a length ranging from 50 nm to 500 nm.

The porous material can have at least one diffraction peak in an angle domain corresponding to a structural period of 1 nm or more in X-ray diffraction method.

Further features of the present invention will become apparent from the following description of exemplary embodiments with reference to the attached drawings.

DESCRIPTION OF THE EMBODIMENTS

The present inventors used a porous material such as mesoporous silica as an immobilizing support of a biological material such as a protein and found an effect of enhancing the relative activity of the biological material severalfold after heat treatment as compared with that before the heat treatment although the biological material was heated to the optimal temperature and above inherent thereto. Hereinbelow, preferred embodiments of the present invention are described.

The apparatus according to the present invention is an apparatus comprising a porous material having mesopores, a biological material immobilized on the pore wall surface forming the mesopores and a heating unit for heating the biological material. The process for activating a biological material according to the present invention comprises providing a porous material having mesopores, immobilizing a biological material on the pore wall surface forming the mesopores and enhancing the relative activity of the biological material by heating the porous material on which the biological material is immobilized at the optimal temperature and above of the biological material. The present invention uses a porous material, a biological material and a heating unit. The present invention is achieved by providing a porous material, immobilizing a biological material on the porous material, and heating the complex of the porous material and the biological material immobilized on the porous material. Hereinbelow, these constitution features are described one by one. First, the porous material is described.

(Porous Material in the Present Invention)

Figure 1A:
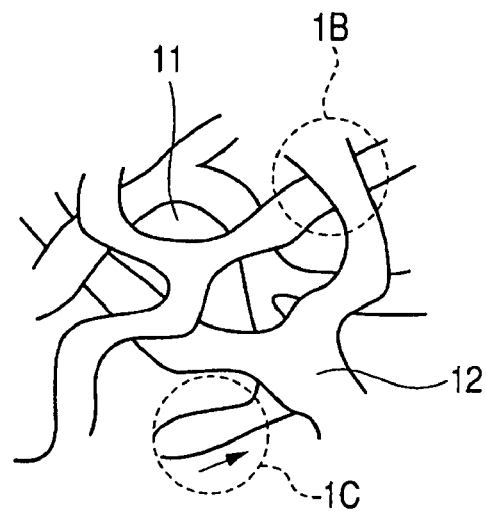
FIGS. 1A, 1B and 1C are schematic views of the porous material of the present invention.
Figure 1B:
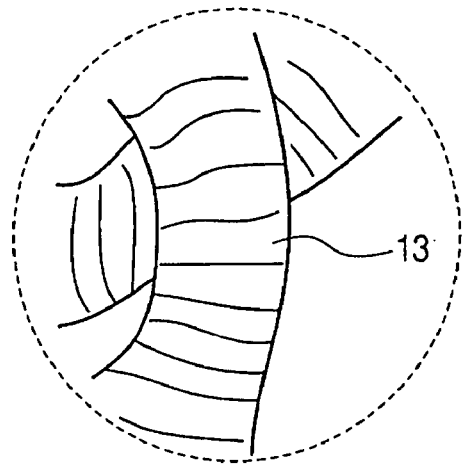
Figure 1C:
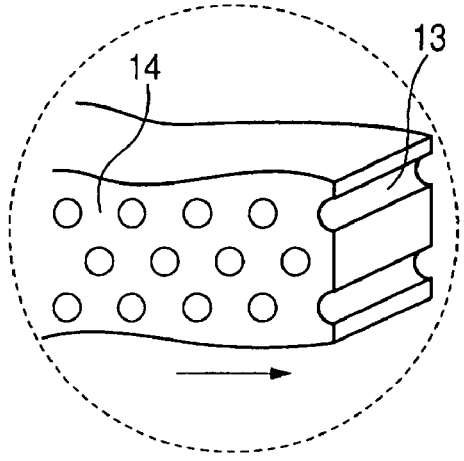

FIGS. 1A, 1B and 1C are schematic views of the porous material of the present invention. The porous material of the present invention comprises dendritic structure 12 constituting a solid part of the porous material and macropores 11 having a relatively large opening defined by the dendritic structure 12. In the porous material of the present invention, the dendritic structure 12 has pore wall 14 constituting the solid part of the dendritic structure 12 and mesopores 13 defined by the pore wall 14.

The shape of the porous material of the present invention is not particularly limited and examples thereof include particulate, spherical and stick-like forms, and, for example, the porous material may be a dendritic structure (dendritic structure 12) illustrated in FIGS. 1A, 1B and 1C. Such a dendritic form is preferable since macropores 11 are formed resulting in excellent internal diffusion.

In the porous material in the present invention, mesopores 13 may be configured to be oriented along the minor axis which is in the direction perpendicular to the length of the dendritic structure 12 as shown in FIGS. 1A, 1B and 1C, or may be configured to be oriented along the major axis extending almost in parallel with the length of the dendritic structure 12. When mesopores 13 are configured to be oriented along the minor axis, larger amount of biological material can be immobilize on the porous material. Mesopores 13 may be configured to penetrate the dendritic structure 12 as shown in FIGS. 1A, 1B and 1C. This enables the activity of the biological material effectively to be exhibited when the biological material is immobilized on the pore wall of mesopores 13.

It is preferable that the diameter of mesopores 13 is 2 nm or more and 50 nm or less. When it is less than 2 nm, biological materials cannot be introduced into the mesopores. Meanwhile, when it exceeds 50 nm, the stability of the spacial configuration of the biological material may be deteriorated. As for the diameter of mesopores 13, the distribution of the diameter of the mesopores can have a single maximal value. As for the diameter of mesopores 13, 60% or more of the total number of mesopores can also fall in a range which includes the single maximal value mentioned above and has a width of 10 nm in the distribution of the diameter of mesopores. When this ratio is less than 60%, constant effect cannot be expected due to the variation in the immobilization amount and the activation function, which is not convenient. The distribution of the mesopores can be determined by conventional methods such as Berret-Joyner-Halenda (BJH) method.

The length of the mesopores can be 50 nm or more and 500 nm or less. If the length is less than 50 nm, stabilization effect may not be obtained, and if it exceeds 500 nm, dead zone may be caused by the biological material which is clogged up at or in the vicinity of the entrance of the mesopores so that the mesopores cannot be used effectively, and thus either of the cases is not preferable in the present invention. The length of the mesopores can be determined by the observation using a scanning electron microscope (SEM) or a transmission electron microscope (TEM).

In the porous material in the present invention, mesopores can be disposed regularly. The analytical method by X-ray diffraction (XRD) measurement can be used to confirm that mesopores are disposed regularly. For example, in the porous material in the present invention, if one or more diffraction peaks are present in the angle domain corresponding to the structural period of 1 nm or more, it means that mesopores are disposed regularly.

In the porous material in the present invention, the disposition of mesopores is not particularly limited. For example, as shown in FIGS. 1A, 1B and 1C, the mesopores may be disposed in a honeycomb-packed structure in a cross-section vertical to the orientation direction of the mesopores. The mesopores may be disposed in a cubic structure or three-dimensional hexagonal structure, or may be disposed at random. In particular, the mesopores can be disposed in a honeycomb packed structure from the viewpoint that the relative activity resulted from biological material per unit weight of the structure body of the present invention increases.

(Providing Step of the Porous Material of the Present Invention)

Next, providing step of the porous material of the present invention is described.

No particular limitation is imposed on the providing step of the porous material of the present invention as long as it is a method by which the porous material having the above-mentioned characteristic can be prepared. Examples of such providing step include a sol-gel method using a surfactant, various kinds of organic molecules and a material constituting solid components of the porous material. Hereinbelow, this sol-gel method is described.

At first in the providing step of the porous material of the present invention, a step of reacting a surfactant, organic molecules and a material constituting solid components of the porous material under hydrothermal condition is performed. Temperatures of 100° C. or more and 150° C. or less are exemplified as the reaction temperature. Several hours to several days are exemplified as the reaction time. The reaction temperature and the reaction time may be suitably optimized in accordance with the size and properties of the biological material to be immobilized within the mesopores. An appropriate amount of various kinds of hydrolysis reaction catalysts may be added in the reaction system in accordance with the solid components of the pore wall constituting the porous material. Examples of such a catalyst include commonly used acids such as hydrochloric acid and nitric acid.

In the providing step of the porous material of the present invention, nonionic surfactants such as block copolymers including polyoxyethylene oxide as a hydrophilic group are exemplified as a surfactant, but usable surfactants are not limited to these. In the providing step of the porous material of the present invention, the surfactant forms micelles and thereby constitutes the part which will form mesopores of the porous material. Since the number of associated molecules forming a micelle is constant under certain reaction conditions, pores of the same size may be formed. Spherical, tube-like, layers and so on are exemplified as the shape of the micelle formed by the surfactant but any shape of micelles may be formed in the reaction system.

In the providing step of the porous material of the present invention, the organic molecules are not particularly limited as long as they are materials which can change the association state of the above-mentioned surfactant in the reaction system in various ways. For example, n-decane may be used to form mesopores of the porous material configured to be oriented along the minor axis. However, this is an example by any means and various kinds of materials can be used and the addition amount may be suitably selected.

In the providing step of the porous material of the present invention, the materials constituting the solid components of the porous material are not particularly limited as long as they can constitute the pore wall of the porous material, and examples thereof include halides, chalcogens, alkoxides. Compounds can contain silicon, and various kinds of silanes such as tetraethoxysilane and tetramethoxysilane which are silicon-containing alkoxides are more preferable. For example, organic silica hybrid materials having an organic group containing one or more carbon atoms, two or more silicon atoms which connect to this organic group at two or more sites and one or more oxygen atoms which connect to the silicon atoms are also preferable.

Next in the providing step of the porous material of the present invention, a reaction step under above-mentioned hydrothermal conditions is performed. Then the obtained reaction product is washed with pure water and after that, a step of drying the product naturally in the air is performed. As a result, inorganic-organic composite powder materials containing micelles of the surfactant as a template in the pores are obtained.

Next in the providing step of the porous material of the present invention, a step of removing the surfactant from the thus obtained inorganic-organic composite powder material is performed. This results in a porous material comprising a dendritic structure constituting the solid part and macropores having relatively large openings formed with the dendritic structure. This removing step is not particularly limited as long as it can remove the surfactant without destroying the skeleton of the formed mesopore structure.

The method most generally used as this removing step is a method of calcining the inorganic-organic composite powder materials mentioned above in an oxygen-containing atmosphere. For example, the surfactant can be completely removed without substantial damage on the mesopore skeleton by calcining the powder materials in the air at 550° C. for ten hours. The calcination temperature and time can be optimized in accordance with ingredients forming the pore wall and the surfactant to be used.

As a method for removing the surfactant by a method other than calcining, extraction by a solvent or a removal by a supercritical fluid may be performed. As a method other than calcining and extraction, removal by ozonation can be also performed.

The surface of the pore wall constituting the mesopores in the porous material of the present invention may be coated with various kinds of materials which are different from the constituents of the pore wall in order to provide desired characteristic such as hydrophobicity and low salt content. Examples of such materials include oxides of inorganic metal such as titanium, aluminum, zirconium and tin. Above all, zirconium oxide is preferable as an inorganic oxide in that it easily enables to introduce an oxide film which is different from the oxide surface in the isoelectric point. The term "oxide" as used here refers to a compound having at least one bond between an element such as a metal and oxygen. In order to obtain a coating with such a material, the porous material provided as above may be dipped in an aqueous solution containing the above-mentioned inorganic oxide at a certain temperature for a certain time period. The term "coating" as used here refers to covering all or part of the surface of the pore wall with the above-mentioned material.

(Biological Material in the Present Invention)

Figure 2A:
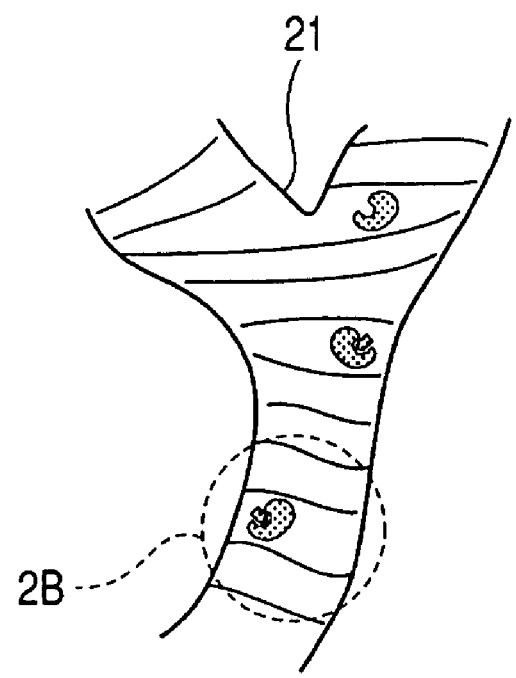
FIGS. 2A and 2B are schematic views of a biological material immobilized on the structure body of the present invention.
Figure 2B:
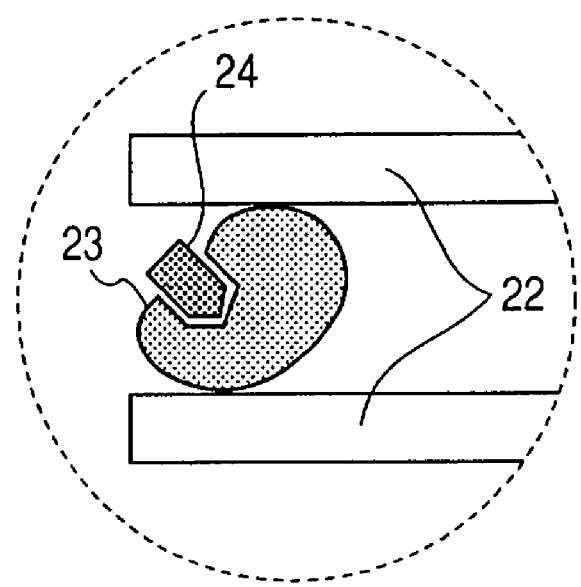

Next, described is a biological material immobilized on the pore wall surface within the structure body of the present invention and in the activation process of the biological material of the present invention. FIGS. 2A and 2B are schematic views of a biological material immobilized on the structure body of the present invention. In this figure, dendritic structure 21 forms the solid part of the above-mentioned porous material and pore wall 22 constitutes the solid part of this dendritic structure. Biological material 23 refers to DNA, protein, enzyme, antigen, etc. and fragment 24 refers to substrate, antigen, antibody, etc. which can specifically bind to this biological material.

In the present invention, proteins such as enzymes are preferably used as a biological material immobilized on the pore wall but the biological material may be a fragment such as a Fab antibody which includes the active sites, and the biological material to be immobilized is not limited in particular. For example, it may be a biological material which is not deactivated and exhibits activity even at high temperatures. Although the substance is permanently deactivated at high temperatures under ordinary conditions, the activity can be enhanced at high temperatures by applying the method of the present invention.

Representative examples of the enzymes to which the process of the present invention can be applied include oxidation-reduction enzymes. Glucose oxidase can be exemplified as an oxidation-reduction enzyme, but the biological material in the present invention is not limited to these.

(Immobilization Step of the Biological Material in the Present Invention)

In the present invention, immobilization step of the biological material is a step of immobilizing a biological material on the pore wall of the porous material provided as described above. This immobilization step is not particularly limited as long as the step can immobilize a biological material on the pore wall of the porous material of the present invention and, for example, a method of dipping the porous material in a solution containing the biological material can be included. In addition, it may be a method of coordinating the object biological material with a linker to immobilize the former directly onto the pore wall surface through covalent bond. When a material different from the constituents of the pore wall is coated on the pore wall of the porous material, the biological material will be immobilized on the pore wall via the material by this immobilization step.

It is preferable that the immobilization between pore wall 22 and biological material 23 is performed by any one of electrostatic interaction, van der waals force, hydrogen bond and covalent bond. Above all, electrostatic bond is preferable since it adsorbs the substance on the surface inside the pore but it is not particularly limited to these.

Pore wall 22 and biological material 23 may be immobilized through an anchor. This anchor may have an effect, for example, to suppress a large structural change of the biological material and maintain the substance in a stable condition.

The constituent of this anchor preferably has a structure basically the same as the mesoporous material. It is particularly preferable that the anchor has a functional group such as a hydroxyl group, an amide group, amino group, a pyridyl group, an urea group, an urethane group, a carboxyl group, a phenolic group, an azo group, a hydroxyl group, a maleimide group, a silane derivative group, an aminoalkylene group to be linked to the biological material. However, the constituent of the anchor is not limited to these.

(Heating Unit in the Present Invention)

Figure 11:
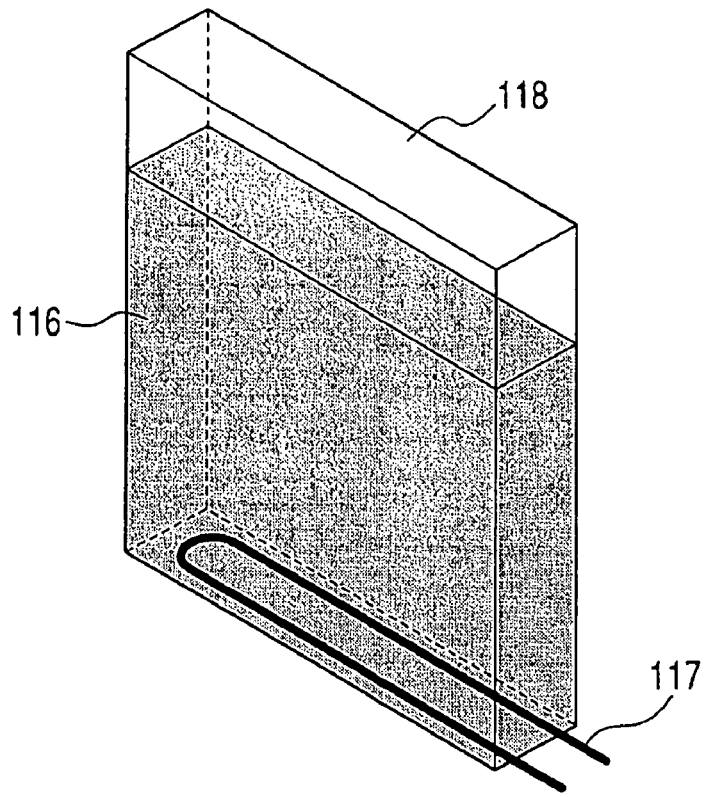
FIG. 11 illustrates an example of the heating unit usable in the present invention.
Figure 12:
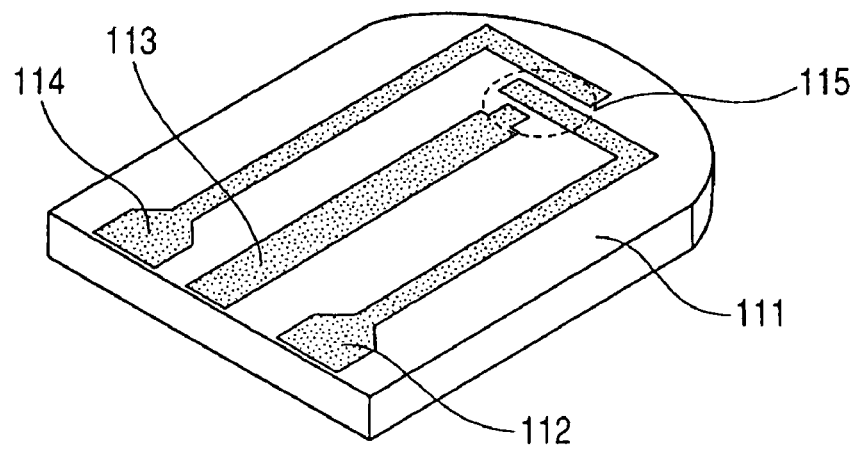
FIG. 12 illustrates an example of the sensor chip useful in an apparatus of the present invention.

An example of the heating unit may have a construction in which heating container 118 containing buffer solution 116 is disposed on electrically heating wire 117 as shown in FIG. 11. It is enabled to heat the biological material with this heating unit. Specifically, a sensor chip as shown in FIG. 12 may be prepared beforehand and the sensor chip and all may be put in the container and heated. The sensor chip has a layer formed by the porous material which carries the biological material.

(Step of Heating the Porous Material in the Present Invention)

In the present invention, the biological material immobilized on the pore wall is heated using the heating unit at the optimal temperature and above of this biological material as described above. It is sufficient that the heating temperature is the optimal temperature and above of the biological material. If the temperature is lower than the optimal temperature of the biological material, the effect of enhancing the relative activity of the biological material cannot be sufficiently obtained. Specific heating temperature varies depending on the kind of the biological material, and, for example, it is 50° C. or more and 90° C. or less when glucose oxidase is used as biological material. When it is lower than 50° C., the relative activity cannot be increased enough. Meanwhile, when it is higher than 90° C., heat causes denaturation and even causes deactivation. The heating time is not limited in particular, but, for example, it is preferably 240 minutes or less, and more preferably it is 120 minutes or less. Such heating results in increase in the relative activity of the biological material after being immobilized on the pore wall for the activity of the biological material as compared that before the immobilization.

EXAMPLES

Example 1

Mesoporous silica having a hierarchical pore structure, that is, porous material having macropores 11 in which substantially uniform tube-shaped mesopores 13 are formed in the direction parallel to the minor axis of the rod, is used in this Example. This is an example of activating this mesoporous silica with immobilized glucose oxidase (abbreviated as GOD, diameter=8.0 nm, IEP=4.6, optimal temperature=37° C.) which is a kind of the oxidation-reduction enzyme at a high temperature.

Synthesis Example 1

2.40 g of triblock copolymer ($EO_{20}PO_{70}EO_{20}$; $HO(CH_2CH_2O)_{20}(CH_2CH(CH_3)O)_{70}(CH_2CH_2O)OH$), a nonionic surface active agent was dissolved in 76.5 mL of pure water. 36 mass % concentrated hydrochloric acid (7.5 mL) was added to this and stirred at room temperature for 30 minutes. Then, 13.9 g of n-decane was added successively and stirred at room temperature for two hours. 0.027 g of $NH_4F$ as a hydrolysis catalyst and 5.10 g of tetraethoxysilane (TEOS) were further added to this mixture and the mixture was used as a precursor solution. The final composition (molar ratio) of the precursor solution is TEOS:HCl:$EO_{20}PO_{70}EO_{20}$:$NH_4F$:n-decane=25:90:0.4:0.7:100.

This precursor solution was stirred at 40° C. for 20 hours and reacted at 120° C. for 48 hours. The obtained white precipitation was sufficiently washed with pure water and vacuum dried.

The obtained powder sample was calcined at 550° C. in the air to decompose and remove the surfactant from within the pores resulting in hollow pores. Removal of organic matters such as surfactant was confirmed by an infrared absorption spectrum.

Figure 3:
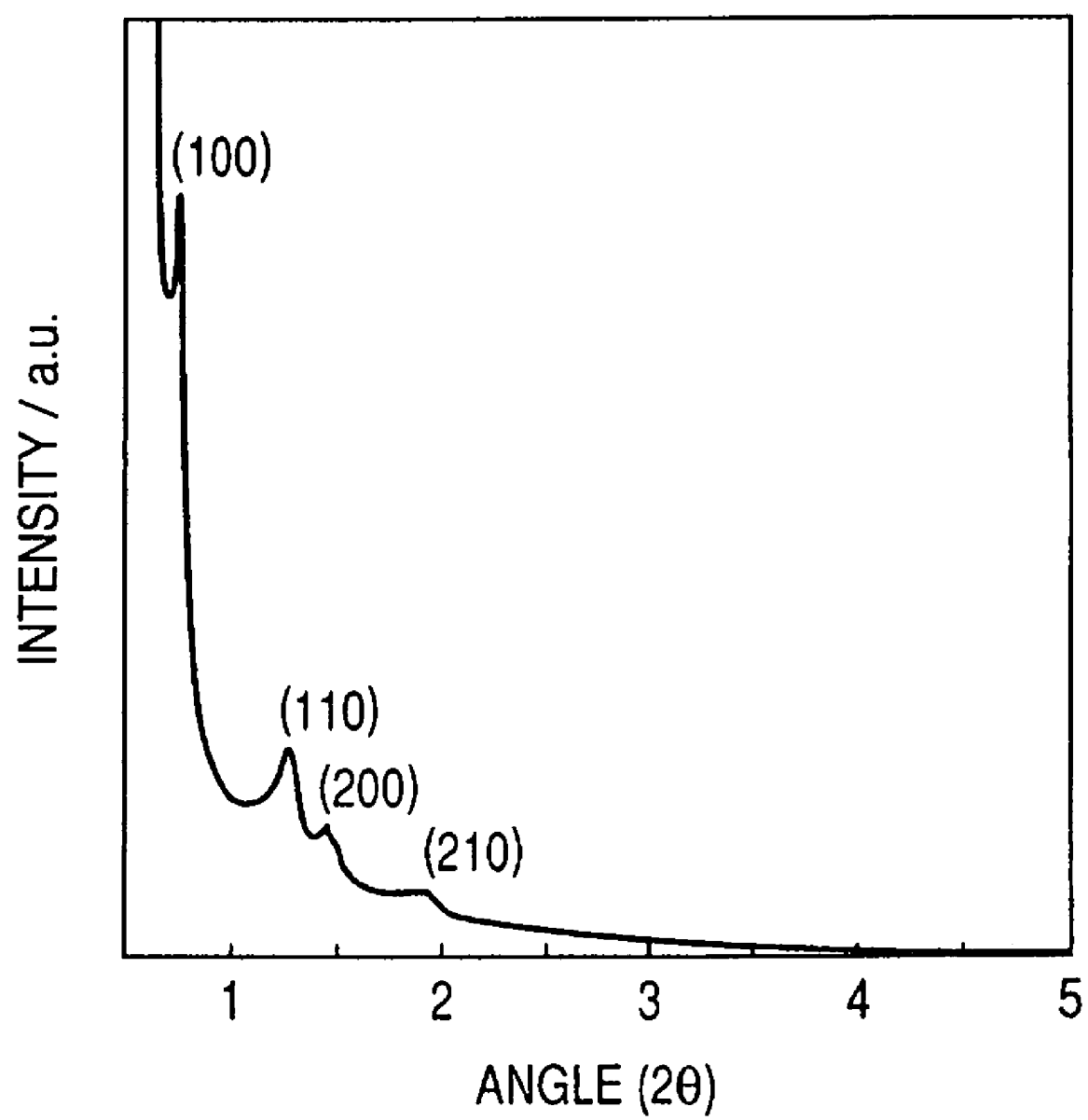
FIG. 3 shows the results of the X-ray diffraction of a hierarchical porous material synthesized in Example 1 of the present invention.

As a result of evaluating the synthesized mesoporous silica powder by X-ray diffraction method, a diffraction peak attributed to (100) face having a hexagonal structure with a face interval of 11.7 nm as well as diffraction peaks attributed to (110), (200) and (210) faces were recognized as shown in FIG. 3. These results show that the pore structure of this mesoporous silica has a hexagonal arrangement with a high regularity.

The thus obtained mesoporous silica powder was subjected to nitrogen adsorption-desorption isotherm measurement at 77K. As a result, the profile of the adsorption isotherm was IV type in the IUPAC classification. The specific surface area determined by B.E.T. method was 700 $m^2/g$, and the pore volume was 1.88 mL/g. Further, pore diameters were calculated by BJH method from the result of this adsorption isotherm and the pore distribution of mesoporous silica synthesized in this example has a narrow distribution having a single peak at 14.3 nm, and about 90% of the pores fell in a range having a width of 10 nm in this distribution.

Figure 4:
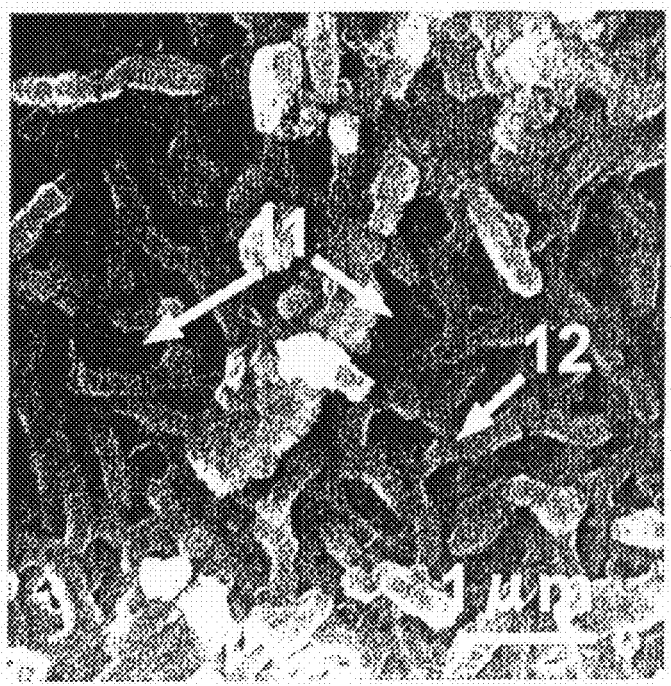
FIG. 4 is a scanning electron microscope image of a hierarchical porous material synthesized in Example 1 of the present invention.
Figure 5:
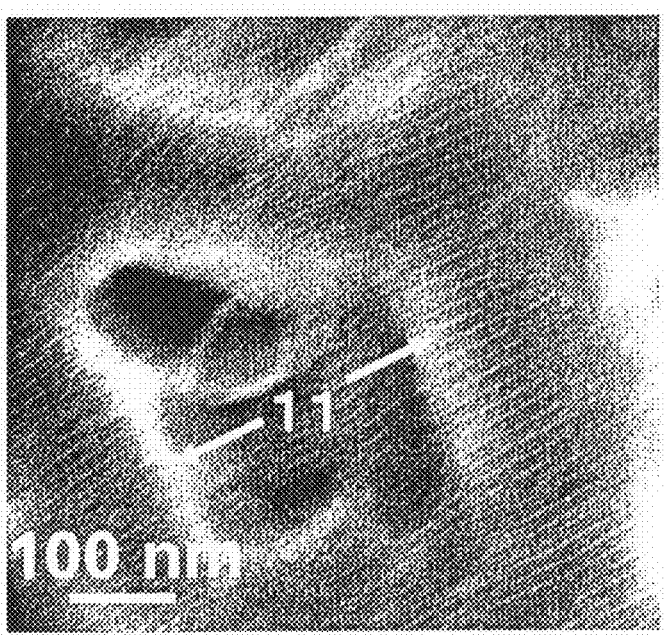
FIG. 5 is a scanning electron microscope image (high power) of a hierarchical porous material synthesized in Example 1 of the present invention.
Figure 6:
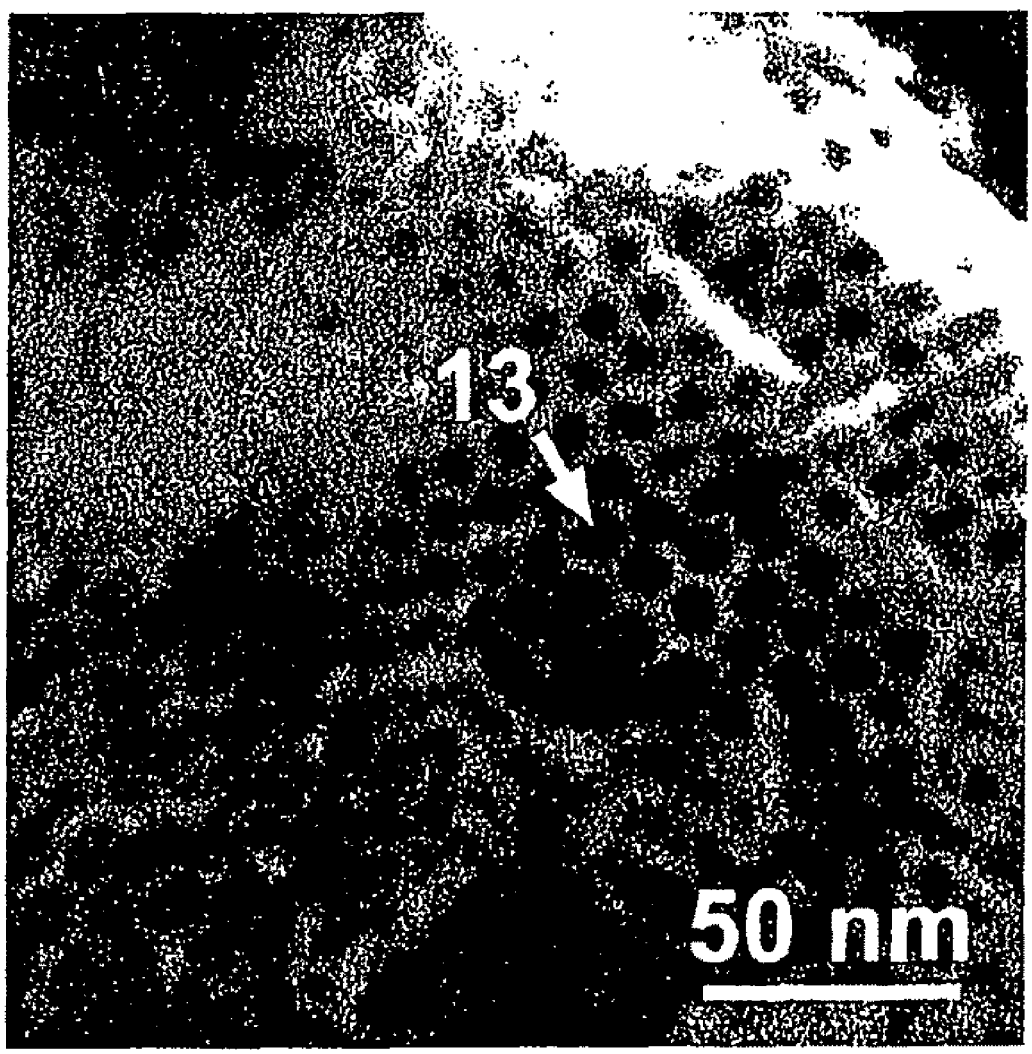
FIG. 6 is a scanning electron microscope image (high power) of a section of a dendritic structure illustrated in FIG. 4.

The powder was then subjected to observation with a scanning electron microscope (SEM) and a structure was observed in which rod-like structure bodies having innumerable branches are disposed in three dimension to form a network as shown in FIG. 4. Macropores of 300-500 nm in the size are formed in the spaces among these branched rod-like structure bodies. Higher power SEM observation revealed that tube-like mesopores 13 having a diameter of 14 nm oriented in the direction along the minor axis of the dendritic structure as shown in FIG. 5. Further, relatively uniform tube-like mesopores 13 formed a honeycomb packed pore structure in the cross section as shown in FIG. 6. Mesopores structure was not destroyed during observation by electron beam.

Synthesis Example 2

Successively, GOD was immobilized within the pores of hierarchical mesoporous silica obtained by Synthesis Example 1 and stabilization effect was measured using oxidative degradation of phenol.

From the relation of the isoelectric points of the silica surface and GOD, GOD were not adsorbed within the mesopores when a buffer solution with pH not less than 5.0 was used. Therefore, 5 mg/mL of GOD was prepared using a 5 mM phosphate buffer of pH=4.0 which was equal to or less than the isoelectric point of GOD, and 10 mg of mesoporous silica obtained by Synthesis Example 1 was added to 1 mL of this GOD solution. This mixture was stirred using a shaker at 4° C. for 20 hours and GOD was immobilized within the mesoporous silica pores. After the adsorption treatment, the mixture was centrifuged at 20,000×g at 4° C. for 10 minutes and GOD-immobilized silica was obtained. Amount of GOD absorbed to the mesoporous silica was calculated using a change at maximal absorption of 280 nm before and after the GOD immobilization treatment in the supernatant solution. As a result of calculation, GOD showed absorbed amount of 150 mg/g or more. Whether the enzyme molecules were introduced into the pore or not was confirmed by the observation with a nitrogen adsorption measuring apparatus that the absorbed amount of the nitrogen molecule to the pore decreased.

Synthesis Example 3

400 μL of 50 mM sodium acetate buffer solution (pH=5.0) was added to 10 mg of GOD immobilized mesoporous silica obtained by Synthesis Example 2, and heated at 50, 70 and 90° C. each for 30, 60, 90 and 120 minutes. After heating, centrifugation was performed and GOD immobilized silica was washed with pure water twice. Then, each of the following was added to the GOD immobilized silica after washing and reacted at 37° C. for 30 minutes.

50 mM Tris-HCl buffer solution (pH=7.5) 400 μL
10% β-D-glucose aqueous solution 100 μL
5000 ppm phenol aqueous solution 8 μL
100 μg/m LHRP solution 100 μL After centrifugation, each of the following was added to 150 μL of the supernatant liquid and stirred, and the absorbance around 500 nm was measured.

1% ferricyanide 150 μL (Prepared with 1M glycine aqueous solution (pH=9.6))
1% 4-aminoantipyrine 300 μL The relative activity with regard to the phenol degradation concentration after 30 minutes was calculated from these results.

Change with time of phenol degradation at 37° C. was measured as above also for the case where the hierarchic mesoporous silica of the present invention having immobilized GOD was used without heat-treatment and the case where an ordinary GOD aqueous solution without immobilization was used.

Figure 7:
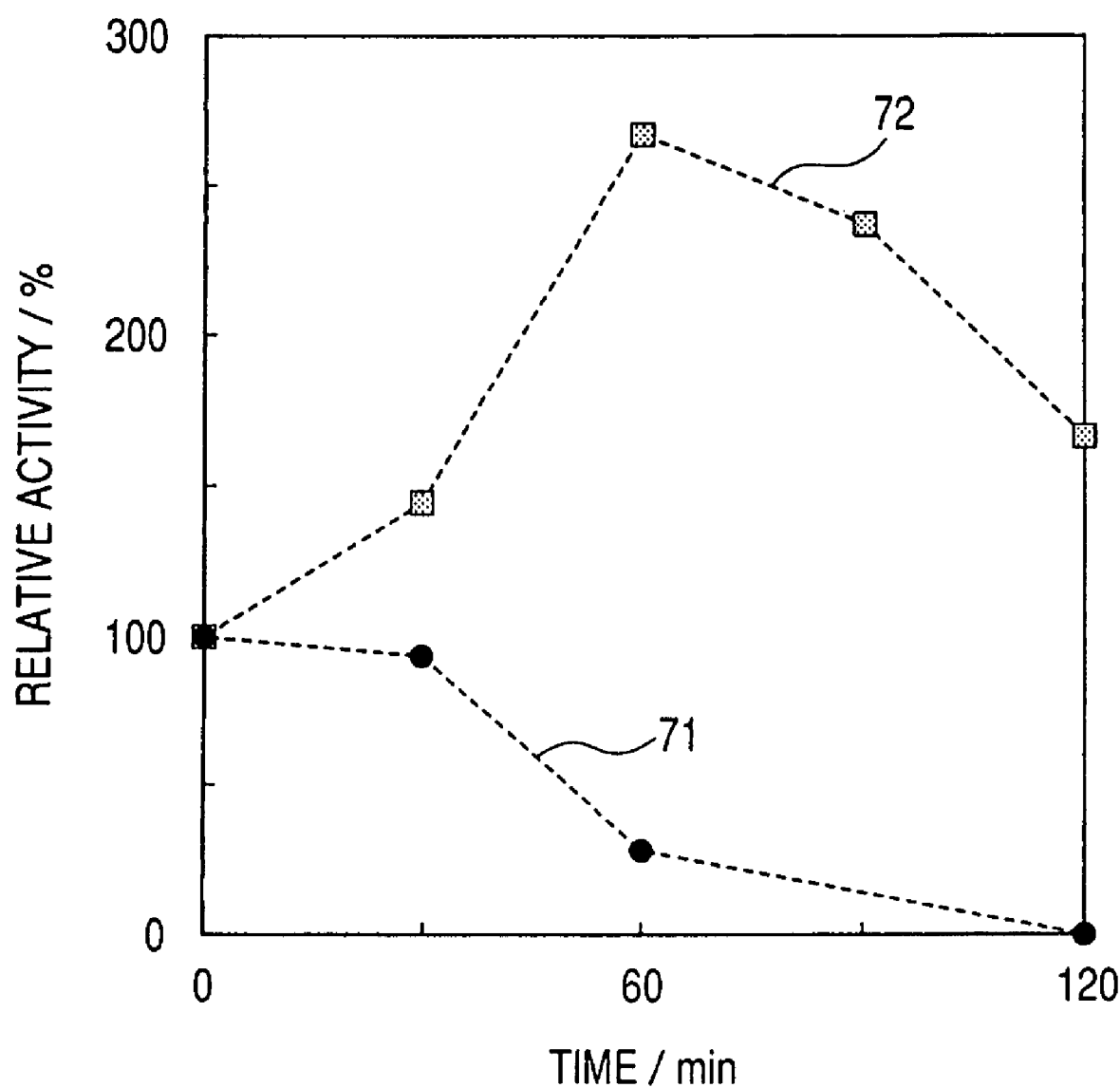
FIG. 7 is a graph showing the change in the relative activity against heat-treatment time when a GOD-immobilized silica obtained in Synthesis Example 3 was heat-treated at 70° C.

FIG. 7 is a graph showing the change in the relative activity against heat-treatment time when a GOD-immobilized silica obtained in Synthesis Example 3 was heat-treated at 70° C. The horizontal axis indicates the duration time (minute) of the heat-treatment whereas the vertical axis indicates the percentage of the value of phenol degradation concentration at each treatment time assuming that the value of phenol degradation concentration obtained by using a GOD-immobilized mesoporous silica heat-treated for 0 minute, i.e. the silica obtained by Synthesis Example 2 is 100%. The relative activity of GOD (● mark indicated by reference numeral 71) which was not immobilized was slowly deactivated by heat-treatment at 70° C. In contrast, the GOD-immobilized silica (■ mark indicated by reference numeral 72) which was obtained by Synthesis Example 3 and heat-treated at 70° C. was confirmed to have a relative activity of 100% or more as well as high stabilization effect against heat. It is appreciated that the relative activity of GOD immobilized within the pores of the mesoporous silica increased by heating at 70° C. The activity showed a value about 3 times more than the initial value by heating for 60 minutes and showed a relative activity which was more than 100% in the case of heating for two hours.

Synthesis Example 4

Synthesis Example 3 was repeated except that the heat-treatment was performed for 240 minutes and change in the relative activity against heat-treatment time was examined on GOD-immobilized silica. The results are shown in FIG. 8.

Figure 8:
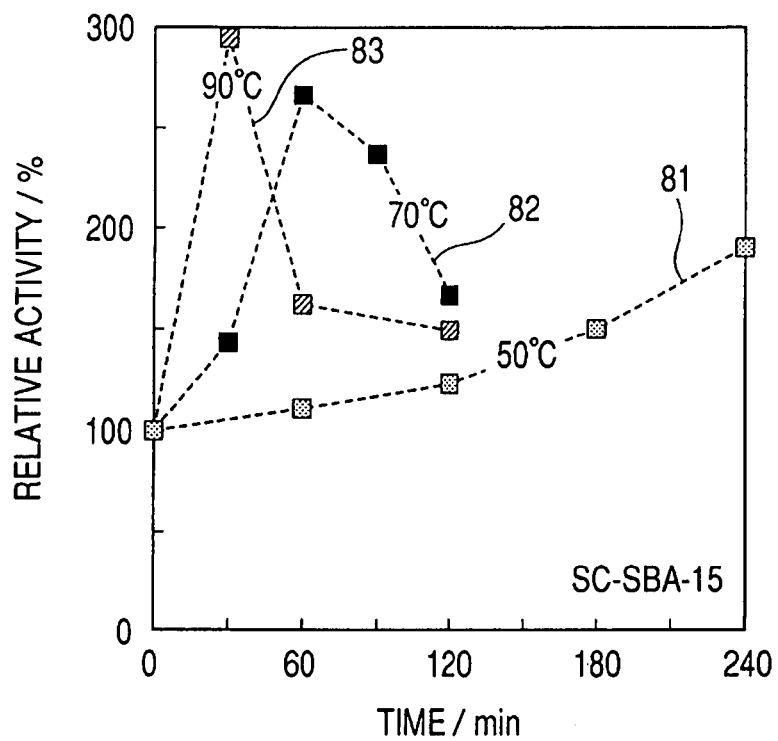
FIG. 8 is a graph showing the change in the relative activity against heat-treatment time when a GOD-immobilized silica obtained in Synthesis Example 4 was heat-treated at 50, 70 and 90° C.

FIG. 8 is a graph showing the change in the relative activity against heat-treatment time when a GOD-immobilized silica obtained in Synthesis Example 4 was heat-treated at 50, 70 and 90° C. (81, 82 and 83). Samples heated at higher temperatures achieved about 3 times more relative activity in a shorter time. It was confirmed that although time needed for the increase in the relative activity varied depending on the heating temperature, high activity was exhibited by heating GOD immobilized in the pores.

Synthesis Example 5

Instead of performing reaction at 37° C. for 30 minutes in Synthesis Example 3, the following treatment was conducted. That is, Synthesis Example 3 was repeated except that after reacted for predetermined time (0 to 240 minutes) at 37° C., centrifugation was performed, supernatant liquid was discarded and the residue was added with 400 μL of 50 mM Tris-HCl buffer solution and heated at 70° C. for 15 minutes. Enzyme activity of GOD per unit hour was determined.

Initial activity was the highest, and the relative activity decreased with passage of time. However, the relative activity increased after heating at 70° C. Similar reaction was performed as a control using an aqueous solution of GOD which was not immobilized. Increase in the relative activity by heating was not observed.

Example 2

This is an example in which GOD was immobilized after the surface of the hierarchical mesoporous silica prepared in Example 1 was modified with an oxide of zirconium and activation by heating was measured as in Example 1.

Synthesis Example 6

10 g of zirconium oxynitrate dihydrate was added to 90 mL of pure water and dissolved at room temperature and 10 mass % of zirconium oxynitrate aqueous solution was prepared. To this solution, the mesoporous silica powder obtained by Synthesis Example 1 was added and immersed for 20 hours. Then the supernatant was removed by centrifugal separation and the residue was washed with pure water three times and dried at room temperature.

The thus obtained hierarchical mesoporous silica modified with Zr was evaluated by X-ray diffraction method. As a result, substantially the same diffraction pattern as that before the modification was shown and it was confirmed that the periodic structure of mesopores was not broken. In addition, as a result of measuring a chemical bond state of the silica surface with X-ray photoelectron spectroscopy analysis (XPS), a peak caused by Zr—O was confirmed, and it was confirmed that the zirconium oxide layer confirmed was formed on the silica surface.

Synthesis Example 7

Successively, GOD was immobilized within the pores of hierarchical mesoporous silica obtained by Synthesis Example 6 and stabilization effect was measured using oxidative degradation of phenol.

In Synthesis Example 2, 5 mM phosphate buffer (pH=5.0) was used in place of 5 mM phosphate buffer (pH=4.0), and the hierarchical mesoporous silica modified with Zr obtained by Synthesis Example 6 was used in place of the mesoporous silica obtained by Synthesis Example 1. Synthesis Example 2 was repeated except these changes and GOD-immobilized Zr-modified mesoporous silica was obtained. The absorbed amount of GOD in this silica was determined and GOD showed absorbed amount more than 120 mg/g. GOD adsorption was substantially not observed in a buffer solution of this pH in the case of mesoporous silica not treated with Zr.

Synthesis Example 8

In Synthesis Example 3, GOD-immobilized Zr-modified mesoporous silica obtained by Synthesis Example 7 was used in place of GOD-immobilized mesoporous silica obtained by Synthesis Example 2. In addition, 50 mM sodium acetate buffer (pH=5.0) was used in place of 50 mM sodium acetate buffer (pH=4.0). Synthesis Example 3 was repeated except these changes and the relative activity for the phenol degradation concentration after 30 minutes was determined. The results are shown in FIG. 9.

Figure 9:
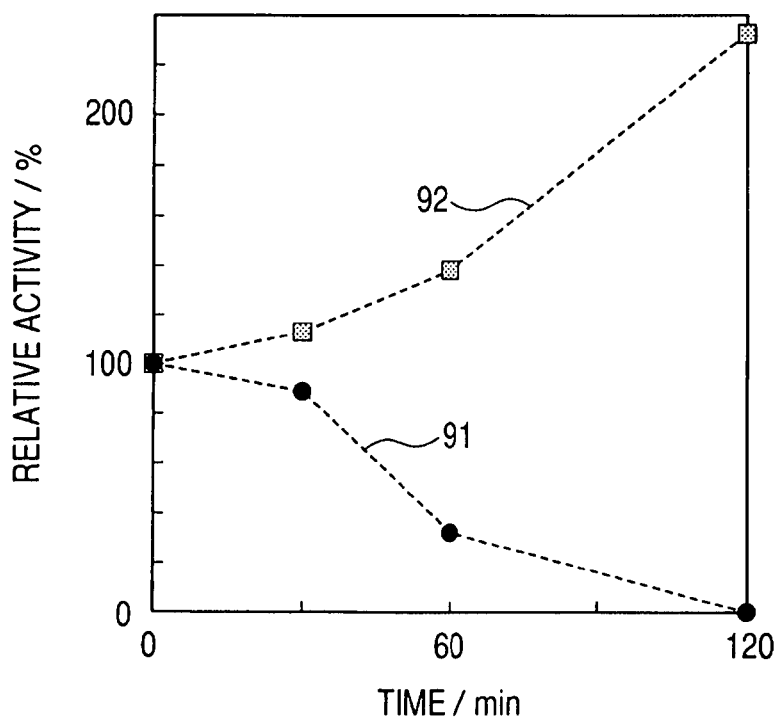
FIG. 9 is a graph showing the change in the relative activity against heat-treatment time when a GOD-immobilized zirconium modified mesoporous silica obtained in Synthesis Example 8 was heat-treated at 70° C.

FIG. 9 is a graph showing the change in the relative activity against heat-treatment time when a GOD-immobilized zirconium modified mesoporous silica obtained in Synthesis Example 8 was heat-treated at 70° C. The relative activity of GOD 91 which was not immobilized was slowly deactivated by heat-treatment at 70° C. In contrast, GOD 92, which was immobilized on a GOD-immobilized zirconium modified mesoporous silica, exhibited remarked increase in the relative activity at 70° C. as in Example 1 and high stabilization effect against heat was confirmed.

Comparative Example 1

SBA-15 in which tube-like pores were formed in parallel with the major axis of the rod-shaped particle was prepared as comparative example as follows. At first 2.4 g of $EO_{20}PO_{70}EO_{20}$ was dissolved in 84 mL of a hydrochloric acid aqueous solution and stirred at room temperature till this solution became clear. To this solution, 7.2 g of n-decane was added and stirred at room temperature at least for one hour. After that, 0.027 g of $NH_4F$ was added under stirring and then 5.1 g of TEOS (tetraethoxysilane) was added. This mixture was stirred at 313K for 20 hours and then reacted at 373K in an autoclave for 48 hours. The reaction product was collected by filtration and dried in the atmosphere and calcined at 813K for five hours.

The thus obtained SBA-15 was evaluated by X-ray diffraction method as in Synthesis Example 1. As a result, a diffraction peak attributed to (100) face having a hexagonal structure with a face interval of 10.8 nm was confirmed. Nitrogen adsorption isotherm measurement revealed that SBA-15 had a specific surface area of 800 $m^2/g$ and a pore diameter of 8.4 nm.

Then, Synthesis Example 2 was repeated except that this SBA-15 was used in place of the hierarchic mesoporous silica of obtained by Synthesis Example 1 to obtain a GOD-immobilized silica for comparison, and the thus obtained GOD-immobilized silica for comparison was subjected to GOD adsorption test. The results showed that the absorbed amount of GOD was 25 mg/g, which was ⅕ smaller absorbed amount than Example 1. It was also found from nitrogen adsorption isotherm analysis using a sample after GOD adsorption that pore volume of SBA-15 did not decrease after GOD adsorption as compared with that before adsorption, which means that GOD was substantially not adsorbed within the pores. There is little effect by the pore structure on the adsorption within the pores considering that the average pore diameter of GOD is about 8 nm while that of SBA-15 is 8.4 nm. Therefore, the above difference in the absorbed amount is supposed to be resulted from the difference in the accessibility which is attributed to the difference of the open channel, which is caused by the difference whether the pore structure extends along the major axis or the minor axis.

Synthesis Example 3 was repeated except this GOD-immobilized silica for comparison was used in place of GOD-immobilized mesoporous silica obtained by Synthesis Example 2 and the relative activity for the phenol degradation concentration was determined. The results are shown in FIG. 10.

Figure 10:
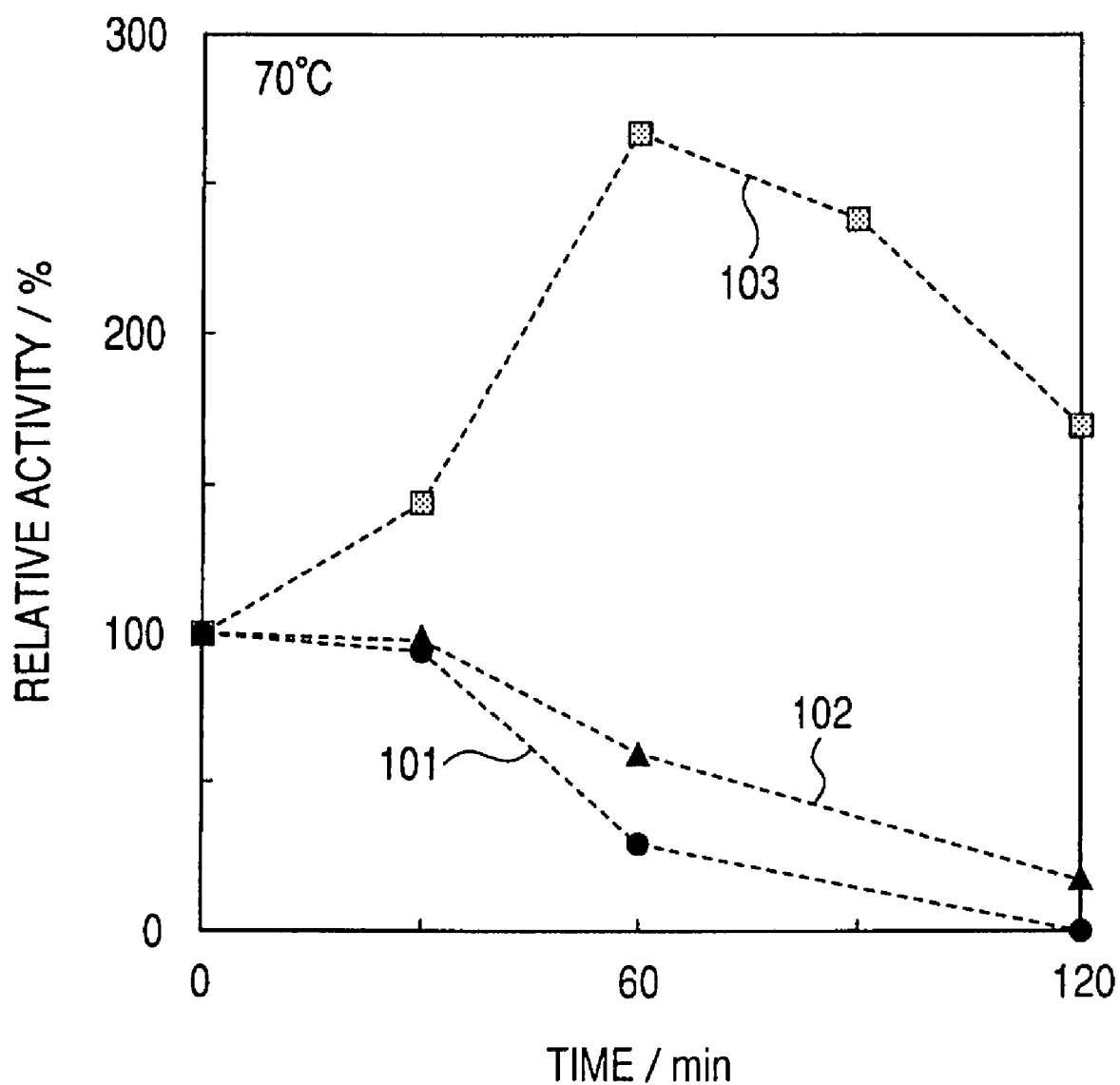
FIG. 10 is a graph showing the change in the relative activity against heat-treatment time when a GOD-immobilized silica for comparison obtained in Comparative Example 1 was heat-treated at 70° C.

FIG. 10 is a graph showing the change in the relative activity against heat-treatment time when a GOD-immobilized silica for comparison obtained in Comparative Example 1 was heat-treated at 70° C. Plot 101 indicates GOD not immobilized, plot 102 indicates GOD-immobilized silica for comparison obtained in Comparative Example 1, and plot 103 indicates GOD-immobilized silica obtained in Synthesis Example 3. As shown in FIG. 10, increase in the relative activity was clearly observed by heating at 70° C. in Example 1, while GOD in this comparative example was deactivated by heating as GOD which was not immobilized. This supports the result of the above adsorption experiment from which is predicted that GOD adheres not within the pores but to the outer surface.

Example 3

This is an example for a biosensor apparatus for measuring glucose concentration having immobilize GOD in the mesopores in a porous material and a heating unit to heat to the optimal temperature and above. As for electrodes, platinum was used for a working electrode and a counter electrode while silver/silver chloride as a reference electrode.

The paste-like hierarchical mesoporous silica synthesized in Example 1 was prepared beforehand. The sensor chip film was formed using a metal mask on glass substrate 111 as shown in FIG. 12. The working electrode is indicated by reference numeral 112, the reference electrode by reference numeral 113, and the opposite electrode by reference numeral 114. The mesoporous silica was applied onto the part 125 on the electrode by squeegee method and dried at room temperature and calcined at 400° C. in the air and the hierarchic mesoporous silica layer 125 was synthesized on the electrode.

GOD was prepared so as to be 5 mg/ml with 20 mM phosphate buffer (pH=4.0), and the prepared mesoporous silica electrode board was immersed in this enzyme solution. The solution was slowly stirred with a shaker at 4° C. for 20 hours to allow GOD to be adsorbed within the mesopores of the mesoporous silica on the electrode. After the reaction finished, centrifugal separation was performed, and GOD-immobilized mesoporous silica on the electrode was washed several times with pure water and a GOD-immobilized electrode was obtained. Then this electrode was immersed in 20 mM phosphate buffer (pH=4.0) and heated at 90° C. with a heating unit shown in FIG. 11 for 30 minutes and washed. Finally, the electrode was immersed in 10 mM ferrocenecarboxylic acid aqueous solution as a mediator of the glucose reaction for 30 minutes and it was adsorbed to the mesoporous silica. The above-mentioned treatment was followed by washing with pure water and the object electrode was obtained. An electrode which was not subjected to the heat treatment at 90° C. was also prepared as a control electrode by a similar method.

The glucose concentration was measured as follows. The voltage was applied to the electrode sweeping from 100 mV to 600 mV and after the oxidation current became constant, the voltage was lowered and a CV curve was obtained. The scanning speed was 1 mV/s. The concentration of the solution of glucose which was the substrate was appropriately adjusted. 10 μL of this glucose solution was dropped onto the mesoporous silica layer on the electrode and the change of the electric current with time was measured. As a result, it was found that the electrode which was heat-treated at 90° C. showed a constant value within around 10 seconds whereas the electrode which was not heat-treated needed time more than 30 seconds.

It was confirmed from the above results that immobilizing GOD within mesoporous silica and heat-treating it at 90° C. in this example enabled manufacturing of a biosensor apparatus which showed a higher GOD activity than the catalytic activity of conventional GOD and enabled measurement/detection in a shorter time by the improvement of the turnover of the enzyme.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2006-159714, filed Jun. 8, 2006, which is hereby incorporated by reference herein in its entirety.

What is claimed is:

1. A process for enhancing the activity of glucose oxidase which comprises the steps of:
   providing a dendritic structure having mesopores configured to be oriented along the minor axis of the dendritic structure which is in the direction perpendicular to the length of the dendritic structure;
   immobilizing the glucose oxidase on a pore wall which forms the mesopores; and
   enhancing the activity of the glucose oxidase by heating the dendritic structure on which the glucose oxidase is immobilized at a temperature ranging from 50° C. to 90° C.

2. The process for enhancing the activity of glucose oxidase according to claim 1, which further comprises the step of coating the surface of the pore wall with a material different from a constituent of the pore wall before the immobilizing step, the different material intervening between the glucose oxidase and the porous wall in the immobilizing step.

3. The process for enhancing the activity of glucose oxidase according to claim 2, wherein the different material is zirconium oxide.

4. The process for enhancing the activity of glucose oxidase according to claim 1, wherein the dendritic structure contains silicon or the dendritic structure consists of silica.

5. The process for enhancing the activity of glucose oxidase according to claim 1, wherein the dendritic structure has at least one diffraction peak in an angle domain corresponding to a structural period of 1 nm or more in X-ray diffraction method.

6. The process for enhancing the activity of glucose oxidase according to claim 1, wherein the immobilization of the glucose oxidase on the pore wall is achieved by any one selected from the group consisting of electrostatic interaction, van der waals force, hydrogen bond and covalent bond.

* * * * *